United States Patent
Ergun et al.

(10) Patent No.: US 7,168,854 B2
(45) Date of Patent: *Jan. 30, 2007

(54) EXAMINATION TABLE PROVIDING X-RAY IMAGING

(75) Inventors: David Lowry Ergun, Verona, WI (US); Richard Franklin Morris, Stoughton, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/872,996

(22) Filed: Jun. 22, 2004

(65) Prior Publication Data

US 2004/0234042 A1 Nov. 25, 2004

Related U.S. Application Data

(63) Continuation-in-part of application No. 10/411,584, filed on Apr. 10, 2003, now abandoned.

(51) Int. Cl.
*A61B 6/04* (2006.01)

(52) U.S. Cl. ............... 378/196; 378/195; 378/208; 378/209

(58) Field of Classification Search .......... 378/195, 378/196, 208, 209; 5/600, 601, 630, 632, 5/633, 634, 635, 648, 649
See application file for complete search history.

(56) References Cited

U.S. PATENT DOCUMENTS

| | | | | |
|---|---|---|---|---|
| 2,534,623 A | * | 12/1950 | Pitts et al. ............... | 5/601 |
| 2,757,997 A | * | 8/1956 | Lee ........................ | 5/601 |
| 3,638,935 A | * | 2/1972 | Lelugas et al. ............ | 5/618 |
| 3,766,384 A | * | 10/1973 | Anderson ................. | 378/209 |
| 3,971,946 A | * | 7/1976 | Craig et al. ............... | 378/195 |
| 4,284,268 A | * | 8/1981 | Gauthier .................. | 5/624 |
| 4,316,298 A | * | 2/1982 | Russo et al. .............. | 5/722 |
| 4,564,861 A | * | 1/1986 | Hishinuma et al. ........ | 250/582 |
| 4,910,386 A | * | 3/1990 | Johnson ................... | 219/385 |
| 5,084,927 A | * | 2/1992 | Parkevich ................. | 5/484 |
| 5,771,272 A | * | 6/1998 | Berger et al. ............. | 378/207 |
| 5,864,146 A | * | 1/1999 | Karellas .................. | 250/581 |
| 6,064,716 A | * | 5/2000 | Siffert et al. .............. | 378/53 |
| 6,081,582 A | * | 6/2000 | Mazess et al. ............ | 378/146 |
| 6,152,598 A | * | 11/2000 | Tomisaki et al. .......... | 378/209 |
| 6,212,714 B1 | * | 4/2001 | Allen et al. ............... | 5/624 |
| 6,320,931 B1 | * | 11/2001 | Arnold .................... | 378/56 |
| 6,322,251 B1 | * | 11/2001 | Ballhaus et al. ........... | 378/209 |

OTHER PUBLICATIONS

Siemens, "UROSKOP® D: A class of its own in urology", 1996.*

* cited by examiner

*Primary Examiner*—Edward J. Glick
*Assistant Examiner*—Chih-Cheng Glen Kao
(74) *Attorney, Agent, or Firm*—Quarles & Brady LLP

(57) ABSTRACT

A multi-use examination table provides x-ray imaging thereby conserving examination room space and to speed patient examination while retaining standard examination table features such as table extensions, foot end drawers, trays and stirrups, and a step for access to the high examination table surface. A repositionable imaging boom allows the table to remain unobstructed when x-ray imaging is not required.

17 Claims, 5 Drawing Sheets

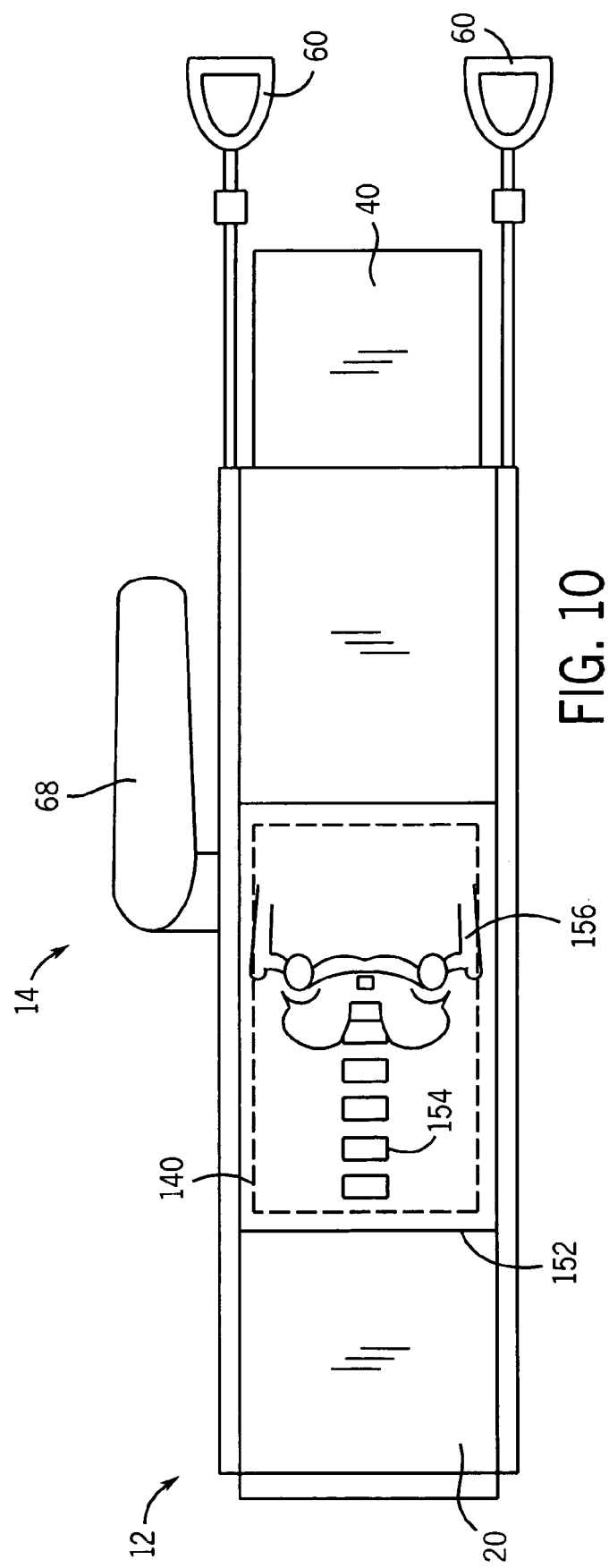

EXAMINATION TABLE PROVIDING X-RAY IMAGING

CROSS-REFERENCE TO RELATED APPLICATIONS

This application is a continuation-in-part of U.S. application Ser. No. 10/411,584 filed Apr. 10, 2003 now abandoned hereby incorporated by reference.

STATEMENT REGARDING FEDERALLY SPONSORED RESEARCH OR DEVELOPMENT

BACKGROUND OF THE INVENTION

The present invention relates generally to examination tables for doctor's offices and in particular to an examination table providing in-office x-ray imaging.

Office space of physicians and other medical practitioners can be limited or expensive so that if an examination function or test is added in-office, an existing faction or text may have to be eliminated from in-office availability. This is particularly true for functions, such as x-ray imaging which normally require equipment that takes up a large portion of floor space of a typical examination room or physician's office. The result is that patients requiring x-rays must be referred to off-site locations or at a minimum different specialized x-ray facilities within the same building, increasing the time required for the patient examination and the inconvenience to the patient.

BRIEF SUMMARY OF THE INVENTION

The present invention provides an x-ray machine that is incorporated into a standard patient examination table to provide either x-ray imaging or unobstructed use of the examination table for normal examination.

By eliminating the need for separate tables, the space required for the x-ray machine is significantly reduced, allowing the x-ray imaging to be instantly accessible in the patient examination room for routine use. Important examination table features: including low cost, small foot print, drawers, stirrups, and table extenders at the foot of the table, and the like, are preserved by limiting the scan area to several compact regions of interest.

BRIEF DESCRIPTION OF THE DRAWINGS

FIG. 10 is a plan view of the top of the table of FIG. 1 showing the x-ray scanning area and relative portions of the patient's skeletal anatomy in phantom.

DETAILED DESCRIPTION OF THE PREFERRED EMBODIMENT

Figure 1:
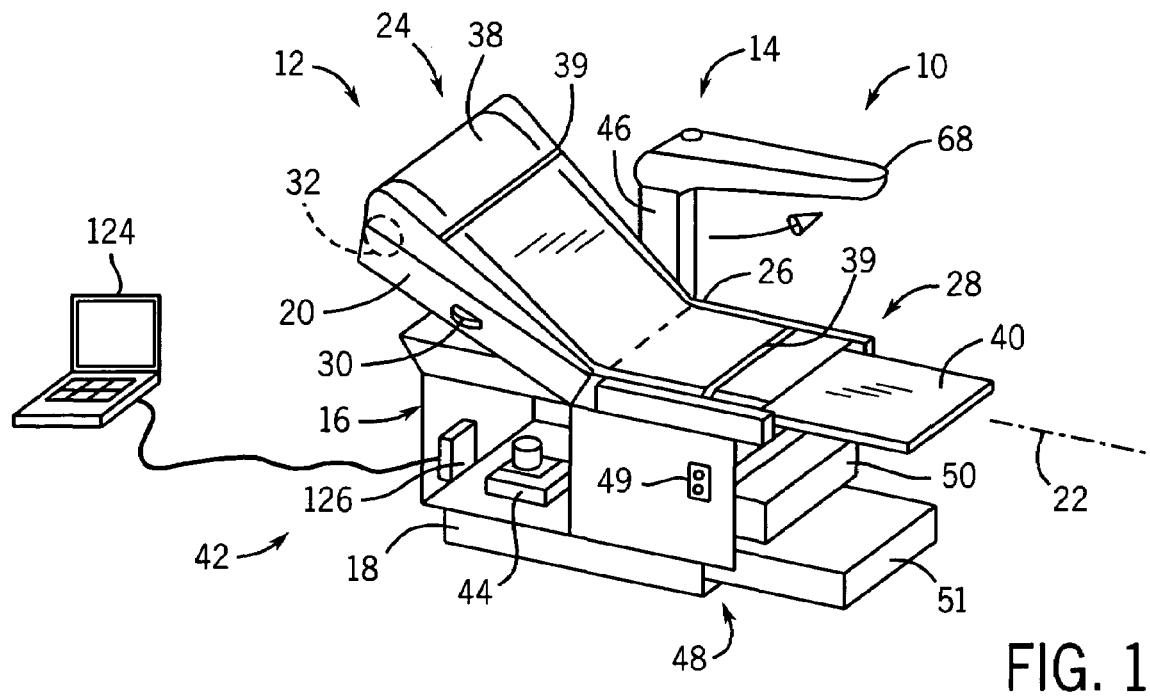
FIG. 1 is a perspective view of an examination table equipped for x-ray imaging showing a C-arm positioned within the pedestal of the examination table providing a pivoting upper arm such as allows unobstructed access to the examination table when x-ray imaging is not required.

Referring now to FIG. 1, a multi-use examination table 10 providing x-ray imaging includes a modified examination table 12 and an imaging arm assembly 14.

The examination table 12 includes a pedestal 16 being a generally rectangular cabinet constructed of sheet metal and having legs 18 for supporting the pedestal 16 on an office floor.

Fitted to the upper surface of the pedestal 16 is a table top 20 extending in a longitudinal direction 22 to receive a patient (not shown) lying on top of the table top 20 also along the longitudinal direction. A head end 24 of the table top 20 may be hinged at transverse hinge line 26 with respect to the foot end 28 of the table top 20 so that the head end 24 may angle upward to support the patient's head and torso at a range of positions between lying down and sitting up. The position of the head end 24 is locked by a release handle 30 according to methods well known in the art. The foot end 28 of the table top 20 remains generally horizontal.

Figure 4:
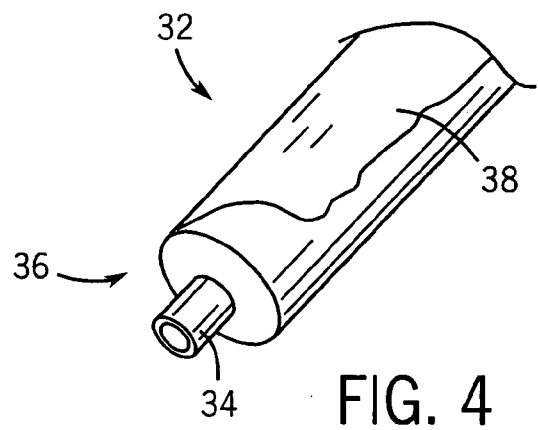
FIG. 4 is a fragmentary view of a paper roll supported at the head of the examination table of FIG. 1.

Referring also to FIG. 4, the head end 24 of the table top 20 may support beneath its upper surface a paper roll dispenser 32. The paper roll dispenser 32 provides an axle 34 fitting within standard hollow-core paper roll 36 so that a sheet of paper 38 may be pulled up over the top of the head end 24 of the table top 20. The paper 38 may be drawn along the surface of the table top 20 in a longitudinal direction to be retained under bands 39 providing a clean surface for each patient.

Figure 2:
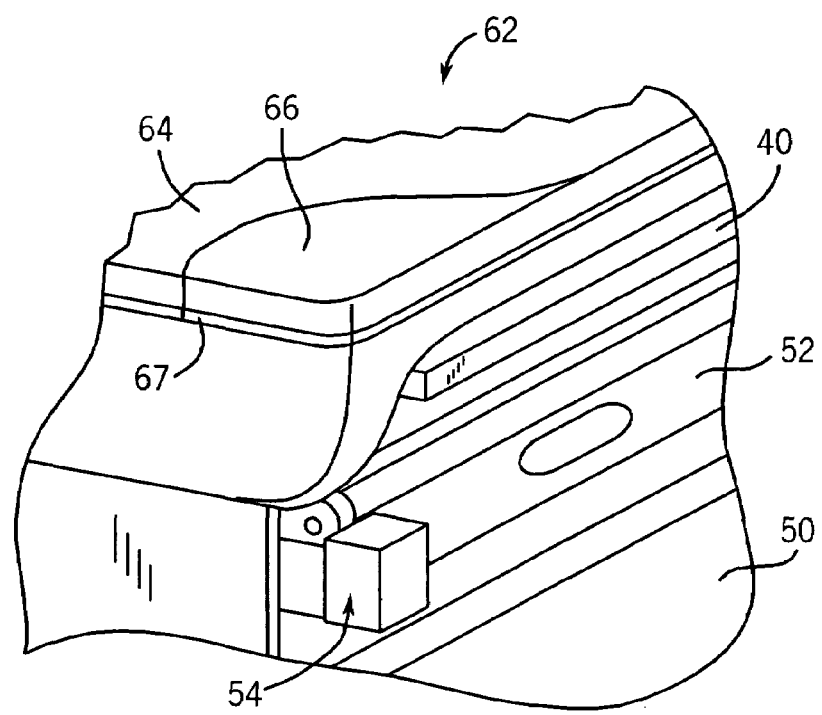
FIG. 2 is a fragmentary perspective view the foot of the table of FIG. 1 showing the upholstered top, the table extension, heated tray, and stirrup in retracted positions.

The length of the table top 20 is less than the maximum expected patient height to provide more space within the examination room. The shortened length of the table top 20 also facilitates the patient's sitting up with his or her legs dangling over the foot end 28 toward the floor and allows the physician to easily maintain eye contact with the patient during the examination. As shown in FIG. 2, if the patient must subsequently lie down, a table extension 40 may be drawn from the foot end 28 of the table top 20 allowing full support of the patient's feet without a great amount of movement of the patient. When retracted, the table extension 40 fits within the foot end 28 of the tabletop.

A head end 42 of the pedestal 16, which in a conventional examination table normally contains drawers, is left empty to support a lower arm of a C-arm 46 being part of the imaging arm assembly 14 as will be described. In contrast, the foot end 48 of the pedestal 16, shown also in FIG. 1, includes a number of longitudinally sliding drawers 50 including, for example, a heated drawer 52 for holding instruments at a temperature near that of body temperature as are well known in the art of examination tables. The drawers 50 may also have liners making them fluid tight.

A step 51 may slide in and out of the pedestal 16, longitudinally in drawer fashion, to allow the patient to climb up onto the table top 20 which unlike radiographic tables is more highly elevated, normally 31 inches above the floor, to facilitate examination.

Figure 3:
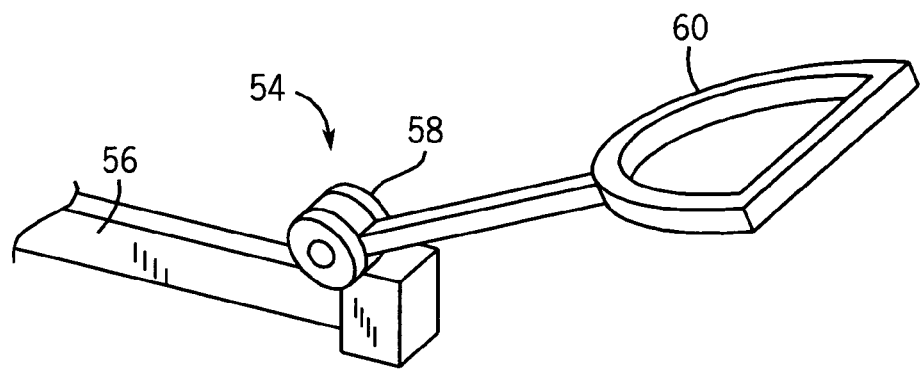
FIG. 3 is a fragmentary view of the stirrup of FIG. 2 in extended position.

Stirrups 54, as also shown in FIG. 3, may extend longitudinally on either side of an upper drawer 50 by means of stirrup extension rods 56 to provide stirrup loops 60 that pivot about pivot axis 58 to receive a patient's feet, also according to methods well known in the art.

The side of the pedestal may support a convenience electrical outlet 49 attached via internal wiring to a source of line voltage.

Fitted to the upper surface of the table top 20, as shown in FIG. 2, and extending its full length between the head end 24 and foot end 28, is upholstery 62 comprised of an internal cushion layer 64, typically of a polyurethane foam, covered by a water-resistant and x-ray transparent outer covering 66. The upholstery 62 is supported by an underlying radio translucent foam-cored, fiber composite 67 a portion of which is shown in FIG. 2.

Figure 5:
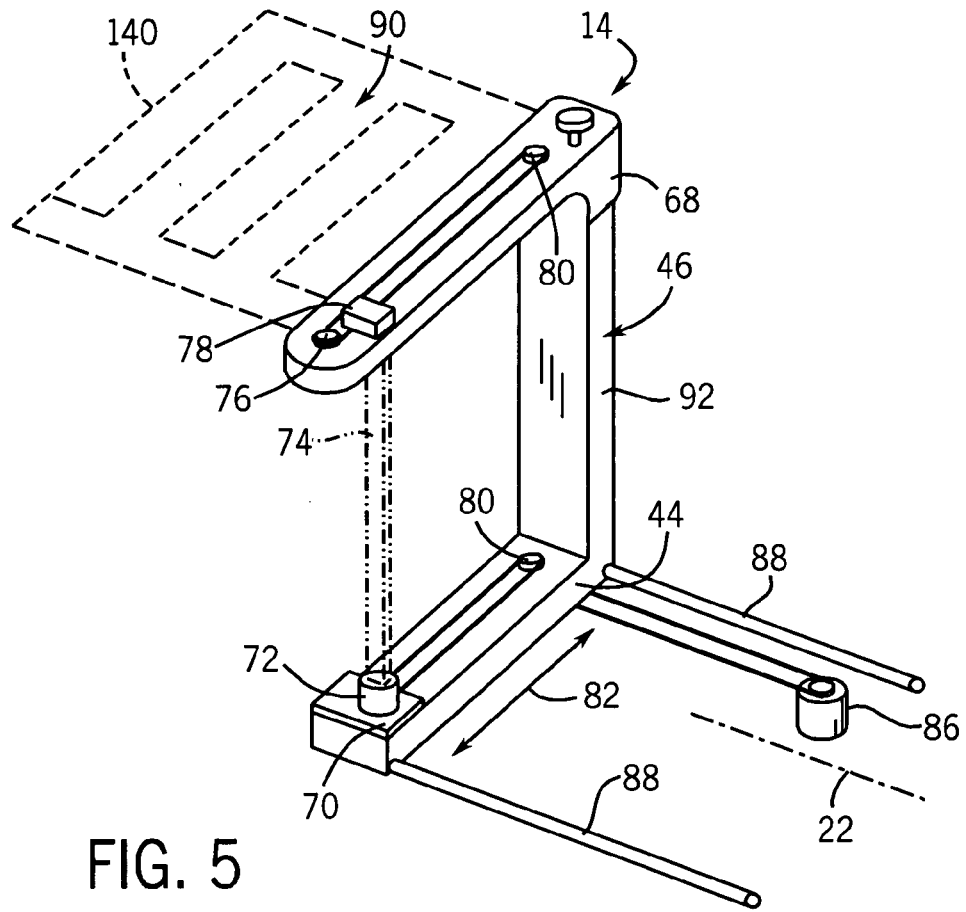
FIG. 5 is a perspective phantom view of the C-arm of FIG. 1 showing an internal mechanism for transverse scanning of the x-ray tube and detector, and an external mechanism for longitudinal scanning of the entire C-arm to obtain a raster pattern.

Referring now to FIGS. 1 and 5, as mentioned above, a lower extension 44 of a C-arm 46 of the imaging arm assembly 14 may fit within the pedestal 16 beneath the head end 24 of the table top 20. A corresponding upper extension 68 of the C-arm 46 may then pivot between a longitudinal stowed position, as shown in FIG. 1, or to a transverse scanning position, as shown in FIG. 5, the latter with upper and lower extensions of the C-arm 46 in aligned opposition about a vertical axis.

The lower extension 44 supports a movable carriage 70 holding an x-ray tube 72 directing a pencil, fan or cone beam 74 of x-rays vertically so as to pass through the head end 24 of the table top 20. Desirably, the end of the lower extension 44 is positioned significantly below the top of the table top 20 when a fan beam is used in order to provide sufficient fan beam width.

The x-ray beam 74 is then intercepted by a corresponding detector 76 on a movable carriage 78 within the upper extension 68 of the C-arm 46. When the C-arm 46 is in the scanning position, carriages 70 and 78 may move in tandem under the influence of servo or stepper motors 80 so that the x-ray beam 74 may scan transversely as indicated by arrow 82 in a lateral direction across a patient supine on table top 20.

An additional stepper motor 86 positioned in the head end 42 of the pedestal 16 allows motion of the entire C-arm 46 on tracks 88 in a longitudinal direction 22. According to conventions in the art, the motion of carriages 78 and 70 and C-arm 46 is coordinated so as to trace out a raster scan 90 having a pitch sufficient to provide continuous coverage of the patient with the x-ray beam 74 over a patient scan area 140. At regular points within the patient scan area 140, dual energy measurements indicating attenuation of the x-ray beam 74 through the patient at two energies.

Figure 6:
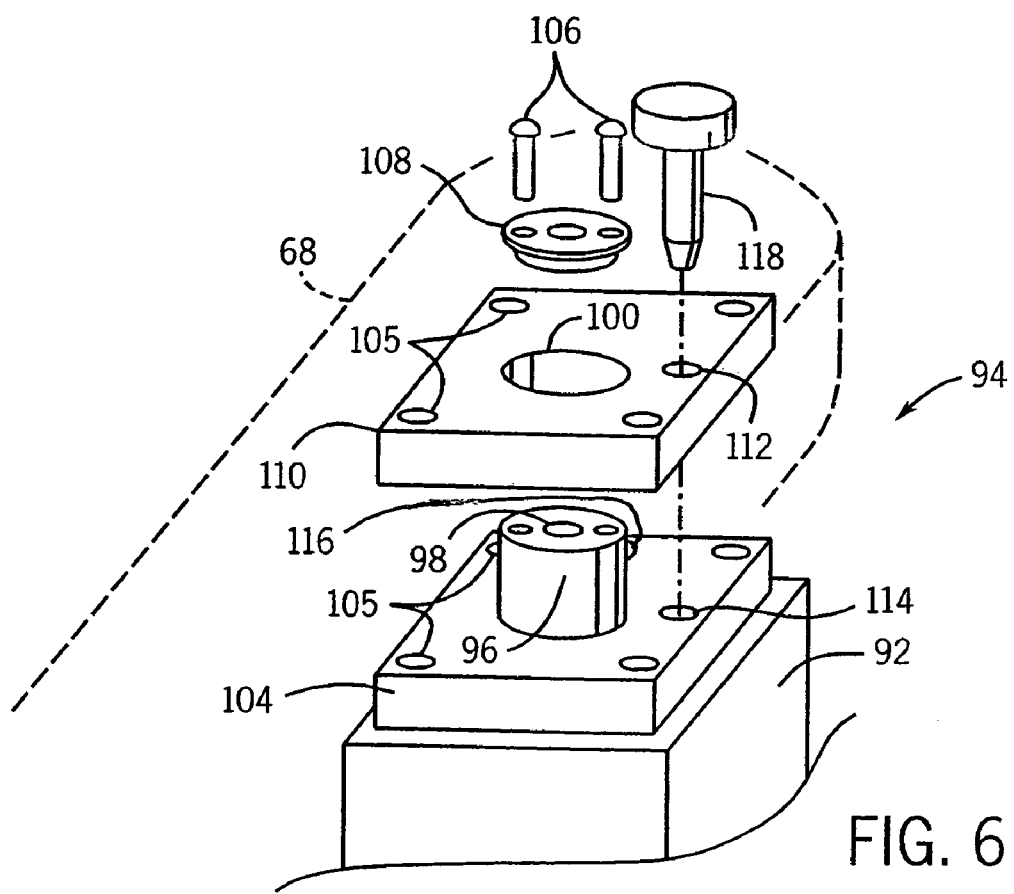
FIG. 6 is an exploded view of a pivot allowing a swinging of the upper arm of the C-arm between a scanning and into a stowed position about a vertical axis.

Referring now the FIGS. 5 and 6, a vertical column 92 of the C-arm 46 joining the upper extension 68 and the lower extension 44 may include at its top end, a pivot joint 94 having a hinge plate 104 from which vertically extends a hinge pin 96. The hinge pin 96 includes a hollow center 98 for passage of electrical cables and the like and is received within a corresponding bore 100 of a hinge plate 110. The hinge plate 110 is thus free to swivel about a vertical axis with respect to the column 92.

The hinge plates 104 and 110 include a number of mounting holes 105 for attaching each to the lower extension 44 and upper extension 68, respectively. Hinge plate 110 may be retained on the hinge pin 96 by cap screws 106 fastening a retainer disk 108 to the hinge pin 96 to sandwich the hinge plate 110 between the hinge plate 104 and the retainer disk 108.

The hinge plate 110 includes a guide hole 112 aligning with a corresponding first guide hole 114 in hinge plate 104, when the upper extension 68 is extending transversely across the patient in a scanning position, and aligning with a corresponding second guide hole 116 spaced 90 degrees from first guide hole 114 when the upper extension 68 is extending longitudinally in a stowed position as shown in FIG. 1.

A locking pin 118 may pass through guide hole 112 and one of guide holes 114 and 116 to hold the arm in the respective positions. In this manner, the C-arm may be configured as shown in FIG. 5 for imaging and, as shown in FIG. 1, to provide unobstructed access to the examination table for other purposes.

Figure 7:
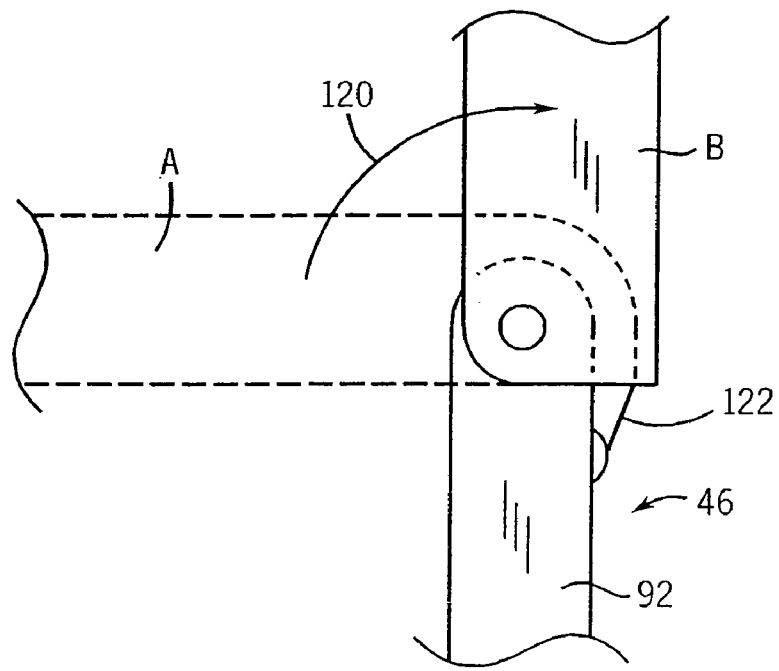
FIG. 7 is a fragmentary side elevation view of an alternative embodiment of the invention in which the upper arm of the C-arm pivots vertically rather than horizontally.

Referring now to FIG. 7, in an alternative embodiment, the upper extension 68 and column 92 of the C-arm 46 may be hinged about a horizontal axis so that the upper extension 68 may move between a horizontal scanning position A and a vertical stowed position B as indicated by arrow 120. A mechanical assist through spring loaded cable 122 may be provided so that the arm is stable in either position A or B, according to methods well known in the mechanical arts.

Referring now to FIG. 1, the imaging arm assembly 14 provides a control terminal 124 and a controller 126 to provide an interface for a doctor to initiate and control the scanning and to receive processed signals derived from the dual energy measurements and relevant to bone health. The control terminal may provide for the execution of a program to provide for simple pre-set techniques (of x-ray current and voltage) for a set of standard imaging situations.

Figure 8:
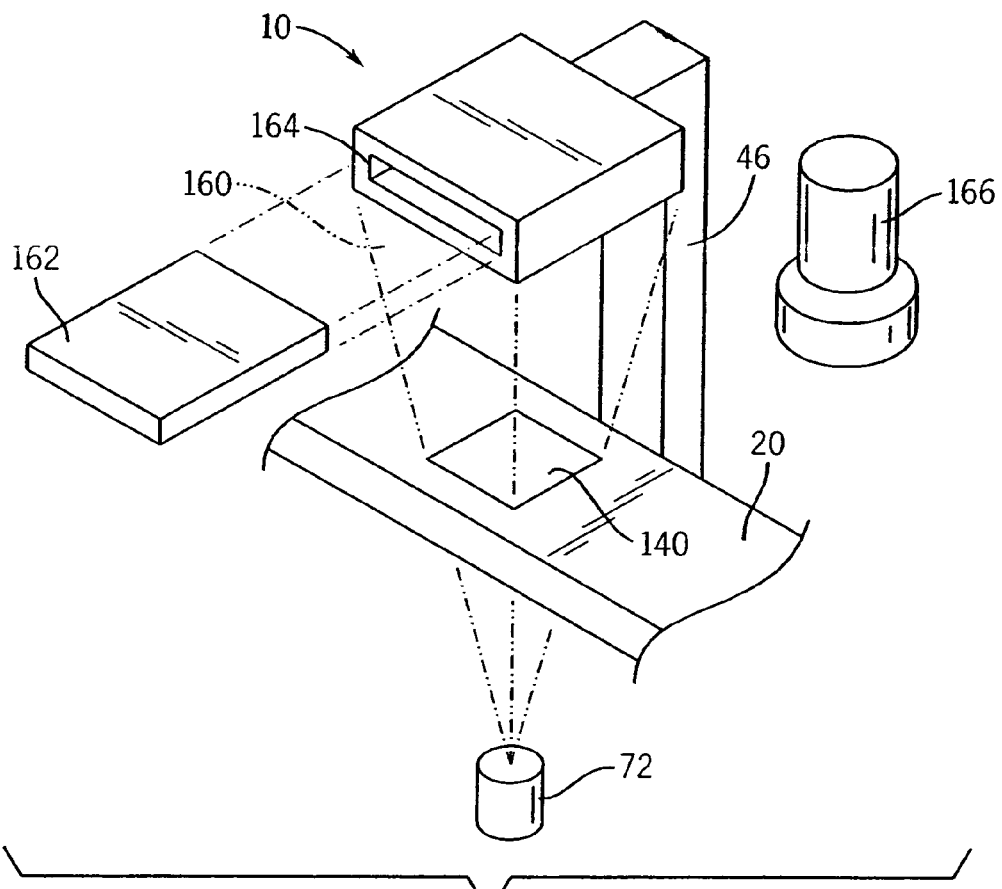
FIG. 8 is a fragmentary perspective view of an alternative embodiment of the examination table using area x-ray detectors.

Referring generally to FIG. 8, in an alternative embodiment, the scanning fan or pencil beam may be replaced with a more conventional area beam x-ray tube 72 positioned as before beneath the table top 20 to project an area beam 160 upward through the upper surface of the table top 20 collimated to the patient scan area 140. The x-ray tube 72 may be a conventional stationary anode or rotating anode tube.

An x-ray cassette 162 either supporting a conventional grid or screen and film or a stimulable phosphor plate may be received in or removed through a slot 164 in the side of a tray held above the table top 20 by upper extension 68. The cassette 162 may employ a Bucky system using a stationary or moving x-ray grid and may open to remove film for processing or for use with a plate reader for a stimulable-phosphor plate.

Alternatively, electronic area detectors, such as an image intensifier/camera system 166 may be used to detect the area beam 160 or a solid state detector array using photo diodes or other detector materials such as cadmium telluride or cadmium zinc telluride (CZT) may be used to detect the area beam 160 and contained in a housing attached to the upper extension 68 and communicating with the control terminal 124 for the output of data for real-time imaging.

Alternatively, the detector 162 or 166 may be placed beneath the top of the table top 20 and the x-ray tube 72 on the upper extension 68 of the C-arm 46. In this case, for these area detectors, movement of the upper extension 68 of the C-arm 46 is not required.

Hybrid areal systems using an areal detector and pencil beam or fan beam of x-ray are also contemplated by the present invention.

Figure 9:
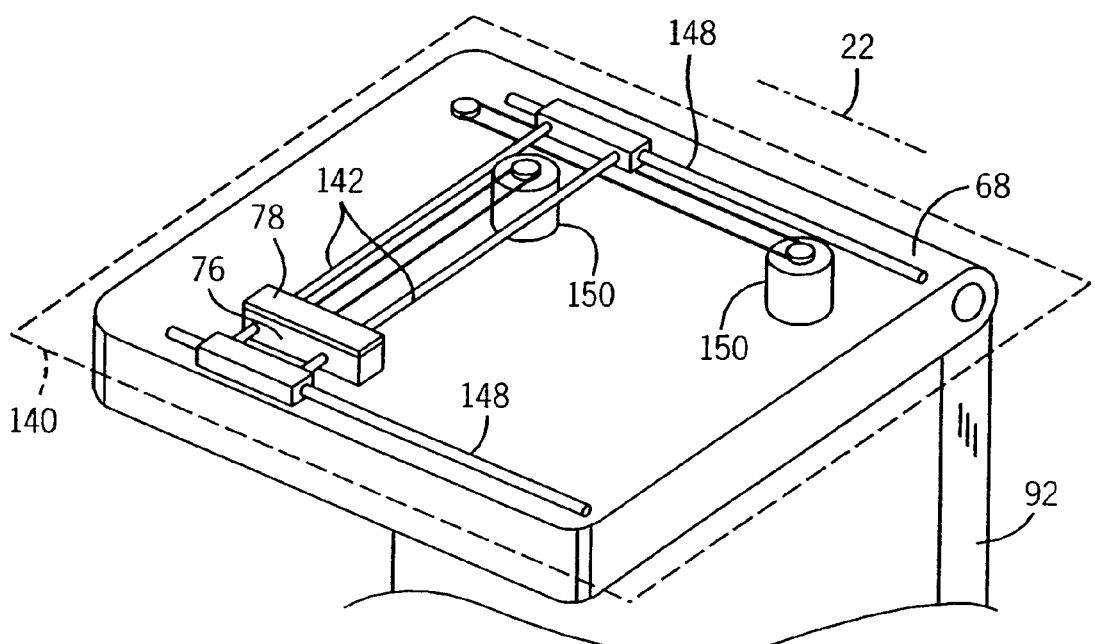
FIG. 9 is a perspective phantom view of an alternative embodiment of the upper arm of the C-arm providing an enlarged housing wholly enclosing the x-ray detector during the longitudinal and transverse scanning.

Referring now to FIG. 9, a housing of the upper extension 68 may be widened along the longitudinal direction 22 so as to enclose the detector 76 and its carriage mechanism 78 throughout an entire raster scan of the patient scan area 140. In this way, mechanical interference between the patient and the detector 76 during the raster scan may be eliminated as well as motion of the C-arm 46. A similar mechanism may support the x-ray tube 72 within the pedestal 16 and coordination of movement of the detector 76 and x-ray tube 72 provided electronically.

Specifically, the upper extension 68 may enclose an x-y track including transverse track 142 allowing for transverse motion of the detector 76 and carriage 78 and longitudinal track 148 providing for longitudinal motion of the track 142 and thus of the detector 76 and carriage 78. Stepper or servo motors 150 may be used to electrically synchronize motion of the x-ray detector 76 with corresponding motion of the x-ray tube 72 in the pedestal 16. In this case, a horizontal axis per FIG. 7 is most conveniently employed to move the upper extension between the scanning and stowed positions.

Referring now to FIG. 10, convenient implementation of the combination of the modified examination table 12 and imaging arm assembly 14 while providing important examination table features is possible by locating and restricting the patient scan area 140 to the head end 24 of the table top 20 above the head end 42 of the pedestal 16. This scanning area may be marked by a visible indication 152 so as to allow a positioning of the patient appropriately for imaging and in particular for scanning of the lower spine 154 and femur scanning 156.

Generally, the patient need not be lying on the table but the table may be used for a patient support, for example, for the patient's arm, during an x-ray procedure.

It is specifically intended that the present invention not be limited to the embodiments and illustrations contained herein, but include modified forms of those embodiments including portions of the embodiments and combinations of elements of different embodiments as come within the scope of the following claims.

We claim:

1. A multi-use examination table comprising:
  a horizontal table unit having a longitudinally opposed head end and a foot end, and a portion that is fixed in a horizontal direction, the table unit including a pedestal supporting a table top that is x-ray transmissive over at least a portion of the table;
  a support arm attached to the table and movable between a first position having a first end in cantilevered transverse extension over the table top and a stowed second position with the first end substantially removed from overhanging obstruction of the table top to allow access to a patient lying on the table top;
  an x-ray source and x-ray detector attached, one on a first mounting at the first end of the arm and one on a second mounting within the head end of the table in substantial vertical opposition to the first mounting when the arm is in the first position, the x-ray source and x-ray detector cooperating to generate x-ray images along an axis through a portion of the patient resting on the table top when the arm is in the first position, the x-ray source and x-ray detector being substantially offset from opposition when the arm is in the second position;
  wherein the foot end of the table includes:
  (i) a step attached to the pedestal to extend from and frilly retract into the pedestal with a longitudinal sliding motion;
  (ii) a table extension section slidably extending longitudinally from and fully retracting longitudinally into a remainder of the table top;
  (iii) foot stirrups slidably extending longitudinally from and fully retracting longitudinally into a remainder of the table top; and
  (iv) at least one drawer extending longitudinally from and fully retracting longitudinally into the pedestal.

2. The multi-use examination table of claim 1 wherein the pedestal is sized to hold an upper surface of the table top at least 30 inches from a floor.

3. The multi-use examination table of claim 1 wherein the drawer is electrically heated to hold examination instruments near body temperature.

4. The multi-use examination table of claim 1 wherein the table top further includes a section for supporting a patient's upper torso, the section for supporting a patient's upper torso raisable in angulation with respect to a remainder of the table top.

5. The multi-use examination table of claim 1 wherein the table top includes a paper roll support holding a paper roll for rotation about a transverse axis at one end of the table top allowing dispensing of paper along a longitudinal axis to cover the table top.

6. The multi-use examination table of claim 1 wherein the pedestal includes an electrical outlet and wiring to attach the electrical outlet to line voltage.

7. The multi-use examination table of claim 1 wherein an upper surface of the table top includes an upholstery layer comprised of an elastomeric foam retained within a water resistant covering.

8. The multi-use examination table of claim 1 wherein the support arm includes a swivel joint having a vertical axis so that the cantilevered portion of the support arm is moveable from a transverse orientation in the first position to a longitudinal orientation displaced to a side of the table top in the second position.

9. The multi-use examination table of claim 1 wherein the support arm includes a swivel joint having a horizontal axis so that the cantilevered portion of the support arm is moveable from a transverse orientation in the first position to a vertical orientation extending upward to a side of the table top in the second position.

10. The multi-use examination table of claim 1 wherein the support arm provides a C-shaped frame having the first and second mountings on opposed ends of the C-shaped frame.

11. The multi-use examination table of claim 1 wherein the first and second mountings are movable by electrically linked servo mechanisms to translate perpendicularly to a vertical axis while in vertical opposition.

12. The multi-use examination table of claim 1 including a motor drive communicating with the support arm to move the support arm for a scanning of the patient.

13. The multi-use examination table of claim 1 including a housing enclosing the first end of the support arm allowing movement within and relative to the housing over a range of scanning.

14. The multi-use examination table of claim 13 wherein the housing is sized to allow movement within and relative to the housing over a range of scanning in two perpendicular horizontal directions.

15. The multi-use examination table of claim 1 wherein the x-ray detector is a removable cassette of a type selected from the group consisting of: a film cassette and a stimulable phosphor plate.

16. The multi-use examination table of claim 1 wherein the detector is an areal electronic detector selected from the group consisting of: a photodiode array, a cadmium zinc telluride array, and an image intensifier/camera unit.

17. The multi-use examination table of claim 1 wherein the table top includes indicia showing the portion of the table that is x-ray transmissive.

\* \* \* \* \*